(12) United States Patent
Chakravarty et al.

(10) Patent No.: US 11,033,205 B2
(45) Date of Patent: Jun. 15, 2021

(54) SYSTEM AND METHOD FOR ANALYZING GAIT AND POSTURAL BALANCE OF A PERSON

(71) Applicant: Tata Consultancy Services Limited, Mumbai (IN)

(72) Inventors: Kingshuk Chakravarty, Kolkata (IN);
Brojeshwar Bhowmick, Kolkata (IN);
Aniruddha Sinha, Kolkata (IN);
Abhijit Das, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 200 days.

(21) Appl. No.: 15/427,762

(22) Filed: Feb. 8, 2017

(65) Prior Publication Data
US 2017/0231532 A1 Aug. 17, 2017

(30) Foreign Application Priority Data
Feb. 12, 2016 (IN) .............................. 201621005052

(51) Int. Cl.
*A61B 5/11* (2006.01)
*A61B 5/00* (2006.01)

(52) U.S. Cl.
CPC ............ *A61B 5/1116* (2013.01); *A61B 5/112* (2013.01); *A61B 5/1122* (2013.01);
(Continued)

(58) Field of Classification Search
CPC ... A61B 5/1116; A61B 5/7203; A61B 5/6897; A61B 5/4595; A61B 5/4023;
(Continued)

(56) References Cited

U.S. PATENT DOCUMENTS

H374 H * 11/1987 Abo-Zena ..................... 342/378
7,988,647 B2 8/2011 Bunn et al.
(Continued)

FOREIGN PATENT DOCUMENTS

CN 104729507 A * 6/2015
WO WO 2014/160451 A1 10/2014

OTHER PUBLICATIONS

Jung-Ah Lee, Sang-Hyun Cho, Young-Jae Lee, Heui-Kyung Yang, Jeong-Whan Lee, J. (Jun. 16, 2009). Portable Activity Monitoring System for Temporal Parameters of Gait Cycles. Retrieved Dec. 10, 2018, from https://link.springer.com/article/10.1007/s10916-009-9311-8. (Year: 2009).*

(Continued)

*Primary Examiner* — Matthew Kremer
*Assistant Examiner* — Samuel C Kim
(74) *Attorney, Agent, or Firm* — Finnegan, Henderson, Farabow, Garrett & Dunner LLP

(57) ABSTRACT

A method and system is provided for finding and analyzing gait parameters and postural balance of a person using a Kinect system. The system is easy to use and can be installed at home as well as in clinic. The system includes a Kinect sensor, a software development kit (SDK) and a processor. The temporal skeleton information obtained from the Kinect sensor to evaluate gait parameters includes stride length, stride time, stance time and swing time. Eigenvector based curvature detection is used to analyze the gait pattern with different speeds. In another embodiment, Eigenvector based curvature detection is employed to detect static single limb stance (SLS) duration along with gait variables for evaluating body balance.

6 Claims, 13 Drawing Sheets

(52) U.S. Cl.
CPC .......... *A61B 5/1128* (2013.01); *A61B 5/4023* (2013.01); *A61B 5/4561* (2013.01); *A61B 5/4595* (2013.01); *A61B 5/6897* (2013.01); *A61B 5/7203* (2013.01)

(58) Field of Classification Search
CPC ..... A61B 5/112; A61B 5/4561; A61B 5/1128; A61B 5/1122
See application file for complete search history.

(56) References Cited

U.S. PATENT DOCUMENTS

| | | | | |
|---|---|---|---|---|
| 9,232,911 | B2 | 1/2016 | Wilson et al. | |
| 2009/0005693 | A1* | 1/2009 | Brauner | A61B 6/508 600/481 |
| 2012/0309532 | A1* | 12/2012 | Ambrus | G06F 3/0425 463/36 |
| 2013/0041291 | A1* | 2/2013 | Soubeyrat | A61B 5/1038 600/595 |
| 2013/0245422 | A1* | 9/2013 | D'arcy | A61B 5/0484 600/409 |
| 2014/0094940 | A1* | 4/2014 | Ghassemzadeh | A61B 5/1117 700/91 |
| 2016/0147959 | A1* | 5/2016 | Mariottini | G06N 5/02 706/46 |
| 2016/0262685 | A1* | 9/2016 | Wagner | A61B 5/1101 |

OTHER PUBLICATIONS

Fredriksson, M. J., Petersson, P., Axelsson, B., & Bylund, D. (Dec. 23, 2009). An automatic peak finding method for LC-MS data using Gaussian second derivative filtering. Retrieved Dec. 10, 2018, from https://onlinelibrary.wiley.com/doi/full/10.1002/jssc.200900395. (Year: 2009).*

EPO Machine translation of CN 104729507A. Provided by EPO. (Year: 2018).*

"Mouser Components Oct. 2006". Screenshot of webpage from Oct. 16, 2006, accessed online, <https://web.archive.org/web/20061016020614/http://www.mouser.com:80/search/default.aspx>. (Year: 2018).*

"static." Merriam-Webster.com. 2019. Retrieved Nov. 21, 2019 from www.merriam-webster.com (Year: 2019).*

* cited by examiner

SYSTEM AND METHOD FOR ANALYZING GAIT AND POSTURAL BALANCE OF A PERSON

CROSS-REFERENCE TO RELATED APPLICATIONS AND PRIORITY

The present application claims priority from Indian provisional specification no. 201621005052 filed on 12Feb. 2016, the complete disclosure of which, in its entirety is herein incorporated by references.

TECHNICAL FIELD

The present application generally relates to the field of gait analysis. More particularly, but not specifically, the disclosure is related to a method and system for finding and analyzing gait parameters and postural balance of a person using a Kinect system.

BACKGROUND

Accurate measurements of temporal and spatial parameters of human gait provide important diagnostic and therapeutic information. It is possible to derive useful information about the quality of life of an individual from his/her gait parameters. It also helps in detecting diseases like Parkinson's disease, osteoarthritis, etc. Gait analysis has a huge importance on neuro-rehabilitation like walking impairments monitoring in adults with stroke. Due to stroke, gait speed and cadence decrease, whereas gait cycle duration and double-limb support time increase. The paretic limb has a longer swing phase and a shorter stance phase compared to the contralateral limb. Gait kinematics can be used for the assessment of patients with stroke. The accuracy of a gait measuring device is a major challenge for its clinical-applicability.

Nowadays a number of systems are being used for assessing the gait quality of the person. Examples include GAITRite electronic mat and Vicon. These systems are generally very costly and requires costly maintenance affairs. Moreover, to operate these sort of expensive and high quality gait labs, dedicated space and well-trained technicians are required. Thus use of gait analysis in clinics is very limited till date. Scarcity of devices is also a major problem faced by patients. In addition, it is not possible to simulate a patient's actual living or mobility requirements in the lab environment. In contrast, solutions based on sensors like accelerometers and gyroscopes, are cheap, lightweight and hence are essentially easily deployable at home. The main disadvantages of such sensors are their inherent susceptibility to gravity, noise and signal drifts. Moreover, these type of solutions impart uneasy feelings for the patients as multiple sensors are to be attached to the body for monitoring. This imposes a huge restriction on the applicability of such technologies in traditional setups.

Similarly, measuring the stance of the person in single limb support is of high importance. Single limb support is a phase in the gait cycle where the body weight is supported by only one limb, while the contra-lateral limb swings forward. This period is limited by opposite toe off and opposite foot strike respectively. During this phase the leg goes from anterior to a posterior position and the hip continues to extend. This phase is mainly responsible for carrying body weight and hence deeply impacts body balance. Shorter periods of single-limb support phase represent poor balance/control during gait arising from various clinical conditions (osteoarthritis, stroke, etc.). As reported in prior studies, the level of pain, function and quality of patient's life with knee osteoarthritis can be determined by measuring the single limb stance. The decreased gait and balance abilities are some of the critical factors that affects daily activities and reduce independence. To evaluate body balance, a separate static exercise is used. In the separate static exercise, a subject or patient is asked to stand on one foot and one leg stance duration is computed as rehab measure. It is defined as static single limb stance (SLS) exercise where static SLS duration is indicative of postural stability.

In order to overcome these challenges, researchers have tried to use Microsoft Kinect™ for unobtrusive gait analysis. Microsoft's Kinect™ is a peripheral device that connects as an external interface to Microsoft's Xbox 360™ or to Microsoft Windows™ computers. The Kinect™ and the associated programmed computer or Xbox sense, recognize, and utilize the user's anthropomorphic form so the user can interact with software and media content without the need for a separate controller. Kinect can be easily installed at patient's residence for gait monitoring. Most of the contemporary Kinect based methods mainly focus on extraction of gait parameters, but they do not present any in depth study on gait variables like single or double limb support.

SUMMARY

Embodiments of the present disclosure present technological improvements as solutions to one or more of the above-mentioned technical problems recognized by the inventors in conventional systems In view of the foregoing, an embodiment herein provides a system for analyzing postural balance of a person. The system comprises a 3D motion sensor, a noise cleaning module, a memory and a processor. The 3D motion sensor captures a skeleton data of the person. The noise cleaning module removes a plurality of noises from the captured skeleton data. The processor is in communication with the memory. The processor is further configured to perform the steps of: tracking ankle coordinates of the person from the captured skeleton data in x plane and y plane; calculating a plurality of gait parameters of the person using the tracked ankle coordinates of the person, wherein the gait parameters are calculated using an eigenvector based curvature analysis; and measuring the static single limb stance (SLS) duration of the person using the plurality of gait parameters, wherein the SLS duration is indicative of the postural balance of the person.

Another embodiment provides a processor implemented method for analyzing postural balance of a person. Initially, a skeleton data of the person is captured using a 3D motion sensor. In the next step, a plurality of noises from the captured skeleton data is removed using a noise cleaning module. Further, the ankle coordinates of the person are tracked from the captured skeleton data in an x-plane and a y-plane. In the next step, a plurality of gait parameters of the person are calculated using the tracked ankle coordinates of the person, wherein the gait parameters are calculated using an eigenvector based curvature analysis. And finally the static single limb stance (SLS) duration of the person is measured using the plurality of gait parameters, wherein the SLS duration is indicative of the postural balance of the person.

Another embodiment provides, a non-transitory computer-readable medium having embodied thereon a computer program for analyzing postural balance of a person.

Initially, a skeleton data of the person is captured using a 3D motion sensor. In the next step, a plurality of noises from the captured skeleton data is removed using a noise cleaning module. Further, the ankle coordinates of the person are tracked from the captured skeleton data in an x-plane and a y-plane. In the next step, a plurality of gait parameters of the person are calculated using the tracked ankle coordinates of the person, wherein the gait parameters are calculated using an eigenvector based curvature analysis. And finally the static single limb stance (SLS) duration of the person is measured using the plurality of gait parameters, wherein the SLS duration is indicative of the postural balance of the person.

It is to be understood that both the foregoing general description and the following detailed description are exemplary and explanatory only and are not restrictive of the invention, as claimed.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and system disclosed. In the drawings.

DETAILED DESCRIPTION OF THE INVENTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Some embodiments of this disclosure, illustrating all its features, will now be discussed in detail. The disclosed embodiments are merely exemplary of the disclosure, which may be embodied in various forms.

Before setting forth the detailed explanation, it is noted that all of the discussion below, regardless of the particular implementation being described, is exemplary in nature, rather than limiting.

Figure 1:
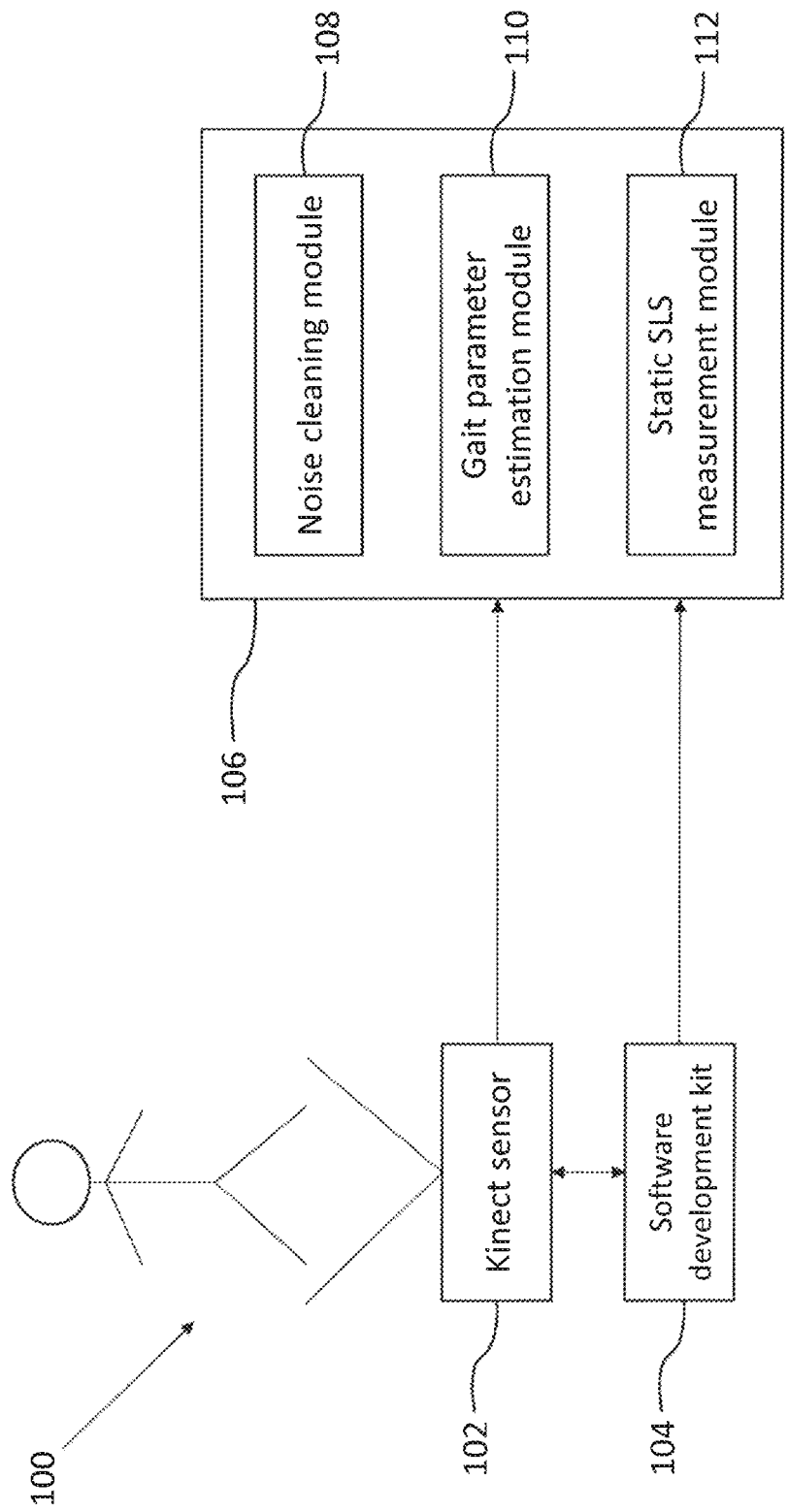
FIG. 1 shows a block diagram of a system for analyzing gait and postural balance of a person, in accordance with an embodiment of the disclosure.

Referring now to the drawings, and more particularly to FIG. 1, where similar reference characters denote corresponding features consistently throughout the figures, there are shown preferred embodiments and these embodiments are described in the context of the following exemplary system and/or method.

In the context of the present disclosure although the present disclosure may be explained with reference to skeleton data received particularly from Microsoft Kinetic™, it may be understood that skeleton data may be received from any motion sensing device. The expressions Kinect™, Kinect™ version1, Kinect™ version2, Kinect may be used interchangeably in the description hereunder to represent the motion sensing device used in an exemplary embodiment; Kinect™ version1 and Kinect™ version2 represent two versions of the Microsoft™ product.

FIG. 1 illustrates a schematic block diagram of a system 100 for analyzing gait and postural balance of a person according to an embodiment of the disclosure. The system 100 is an automatic unobtrusive system configured to measure stride length, stride time, swing time and stance time of the person by only analyzing the spatio-temporal variations of ankle joint data obtained from the Kinect sensor. It should be appreciated that the use of any other motion tracking device or 3D motion sensor which can give us skeleton joint position in 3D world coordinate system is well within the scope of this disclosure. The system 100 is also configured to assess postural control by measuring static single limb support (SLS) duration using Kinect skeleton data.

Figure 2:
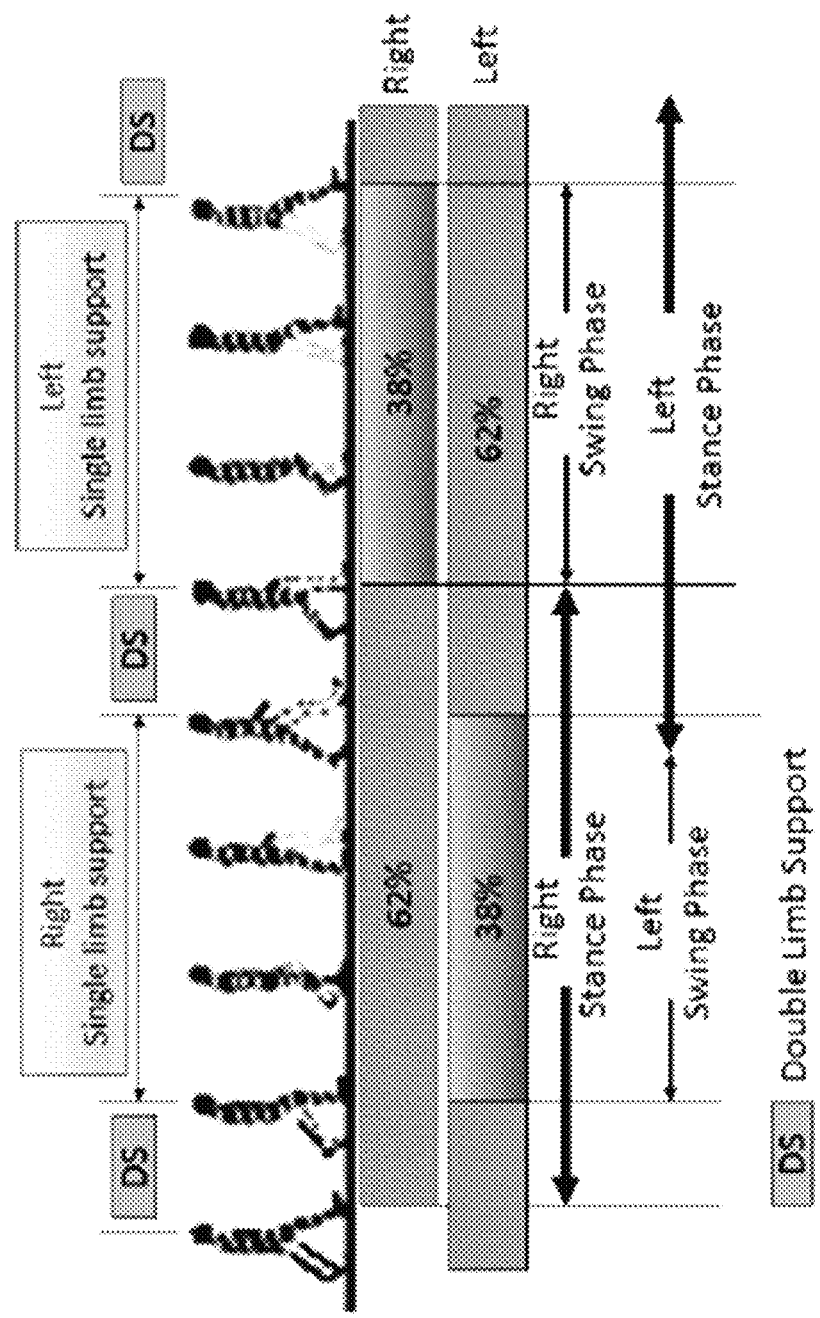
FIG. 2 shows schematic representation of a complete gait cycle of the person, in accordance with an embodiment of the disclosure.

A complete gait cycle of a person with some important intermediate states of gait which need to be analyzed is shown in FIG. 2. Unless otherwise specified all the definitions are general in nature and hold equally well for either left or right leg. Gait cycle: The gait cycle, informally the walking cycle, starts when one leg (left or right) strikes the ground and ends when the same leg touches the ground again. The basic gait cycle includes many phases, of which the two that are of optimum interest under present scenario, are described below: Stance phase: The total duration during which a leg is on the ground. It is typically 62% of the full gait cycle, Swing phase: The total duration (38% of the full gait cycle) during which the foot is off the ground.

Referring to FIG. 1, the system 100 comprises a Kinect sensor 102 or a 3D motion sensor 102, a software development kit (SDK) 104 and a processor 106. The Kinect sensor 102 is in communication with the SDK 104. The processor 106 further comprises a plurality of modules such as a noise cleaning module 108, a gait parameter estimation module 110 and a static SLS measurement module 112.

Figure 3B:
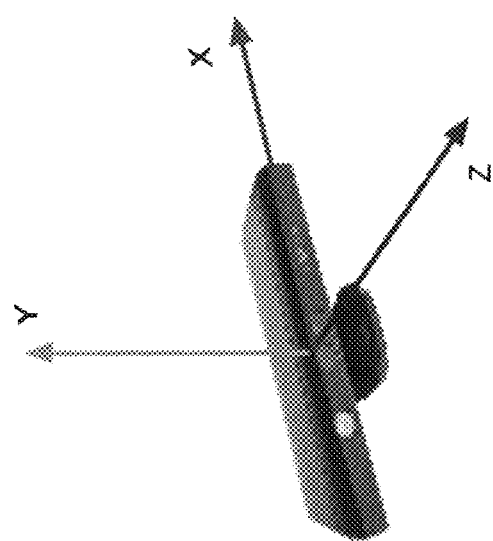
FIG. 3b shows the Kinect coordinate system for recording x, y, z coordinates, in accordance with an embodiment of the disclosure.
Figure 3A:
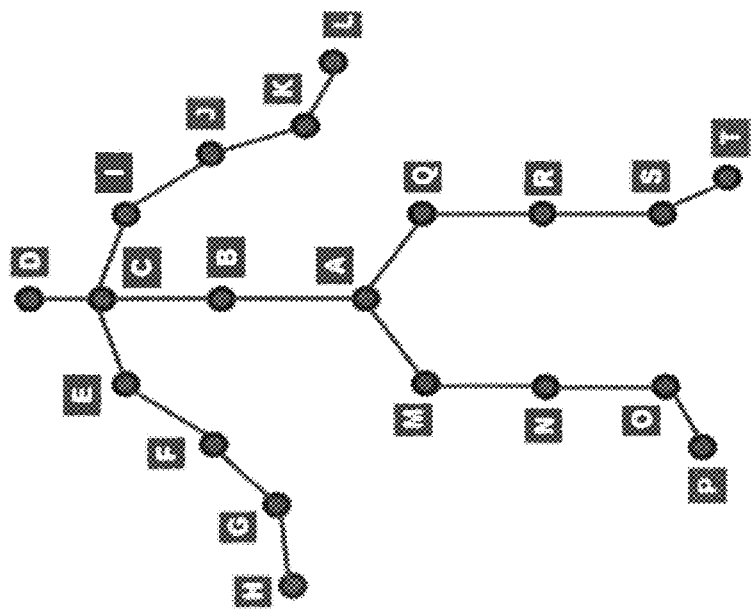
FIG. 3a shows the skeleton model depicting physical connection between joints identified by the Kinect sensor, in accordance with an embodiment of the disclosure.

According to an embodiment of the disclosure, the Microsoft SDK 1.5 is used as software development kit 104. The Kinect sensor 102 and the SDK 104 is used to acquire 3D world coordinates (in meters) or skeleton data of 20 skeleton joints of the person at 30 frames per second. FIG. 3a shows the skeleton model depicting the physical connection between joints identified by the Kinect sensor 102. The SDK 104 mainly records x, y, z coordinates for each joint, along with timestamp, where 'x' and 'y' represent horizontal and vertical direction respectively and 'z' denotes the distance from the Kinect sensor 102 as shown in FIG. 3b. The skeleton data comprises spatio temporal variations of the ankle joint data.

According to an embodiment of the disclosure, the noise cleaning module 108 is configured to remove the plurality of noises from the skeleton data acquired from the person using Kinect sensor 102. The noises in skeleton data is practically visible when the person is completely stationary, but the joint positions recorded by Kinect sensor 102 vary over time. There are many parameters that affect the characteristics and level of noise, which include room lighting, IR interference, subject's distance from Kinect sensor, location of sensor array, quantization, rounding errors introduced during computations etc. In order to get skeleton data cleaned, the skeleton data is converted into a large set of features related to subject's physical structure using the noise cleaning module 108. In each frame, the static features like length of arms, legs, height etc. are computed and the changes are tracked with two previous and two following frames. The data after noise cleaning is used as input to the gait parameter estimation module 110 and the static SLS measurement module 112.

According to an embodiment of the disclosure, the gait parameter estimation module 110 is used to determine various gait parameters. In an example, the gait parameter estimation module 110 estimates stride length, stride time, single limb instance and swing duration. FIG. 2 represents an overview of stance and swing phases in basic gait cycle movements. It is indeed evident from biomechanics that in the process of walking, one limb typically supports the body weight while the other one is advanced in the preparation for its role as the support limb. Initially to capture this phenomena, the left (and right) ankle's x and y-coordinates are tracked over frames.

Figure 4:
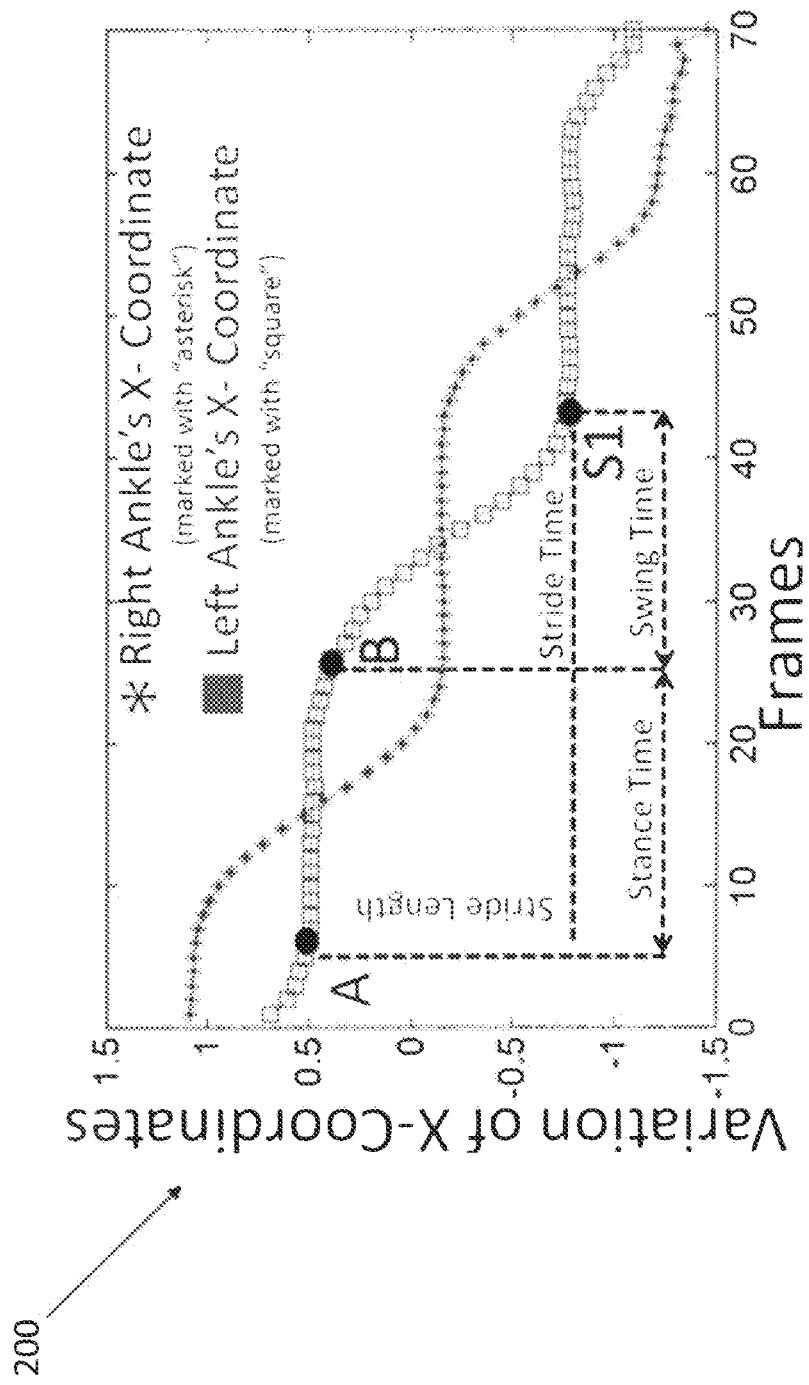
FIG. 4 shows a graphical representation of left and right ankle's variation in X-direction, in accordance with an embodiment of the disclosure.

A graphical representation 200 of left and right ankle's variation in X-direction is shown in FIG. 4 according to an embodiment of the disclosure. As evident in FIG. 4, where left leg comes to momentary rest in the region "A" to "B", as it takes part in aligning and balancing the body weight, while the right leg moves forward. Moreover, FIG. 4 also depicts left and right ankle's horizontal displacement ($X_{AnkleLeft}$) over time (frame). The distance between the heel-points of two consecutive footprints of the same foot is defined as stride length. The time duration of one stride length is called stride time. Hence, the distance and time elapsed between frame "A" to "S1" are considered as stride length and stride time for left leg respectively. One additional observation would be that "A" and "S1" are the two points which eventually indicate the beginning of two consecutive stance phases for left leg.

Figure 5:
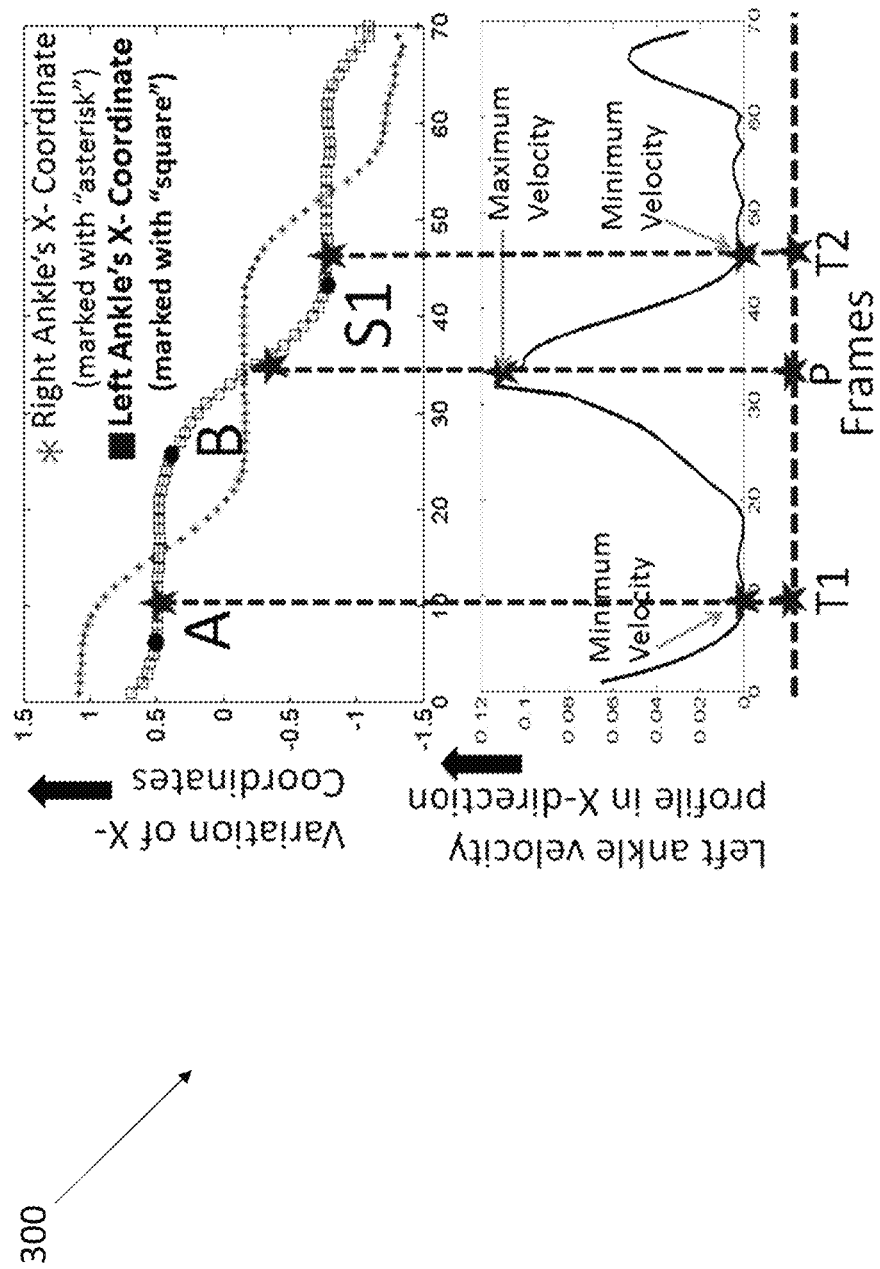
FIG. 5 shows left ankle's velocity profile along with its variation in X-direction, in accordance with an embodiment of the disclosure.

Further, the gait parameter detection module 110 is configured to employ a standard second derivative based curvature detection algorithm to detect two negative curvature points "A" and "S1". The left ankle's velocity profile 300 along with its variation in X-direction is shown in FIG. 5. As it is well known to a person skilled in the art that the ankle attains maximum horizontal velocity during swing phase (between "B" and "S1" as shown in FIG. 5) and almost zero in stance phase (between "A" and "B"). FIG. 5 shows substantial changes in left ankle's velocity $V_{AnkleLeft}$ at point "T1", "T2" and "P". Keeping this fact in mind, the corresponding ankle's (here left ankle) velocity profile have been used to compute the desired curvature points "A" and "S1". Specifically, these points will serve as markers in the proposed method. Before doing curvature analysis, a standard peak and trough detection algorithm is employed to detect peak ("P") and trough ("T1", "T2") regions (points) from the velocity profile as shown in FIG. 5. Finally data points X in region "T1" to "P" and "P" to "T2" are considered for curvature analysis. For this it was assumed that the curvature points will lie in the direction of minimum variance of data. In the next step, covariance matrix $\ddot{X}\ddot{X}^T$ of standardized data $\ddot{X}$ is computed (i.e. $\ddot{X}=X-X'/\sigma$, where $X'$ & $\sigma$ are mean and standard deviation of X respectively).

Figure 6:
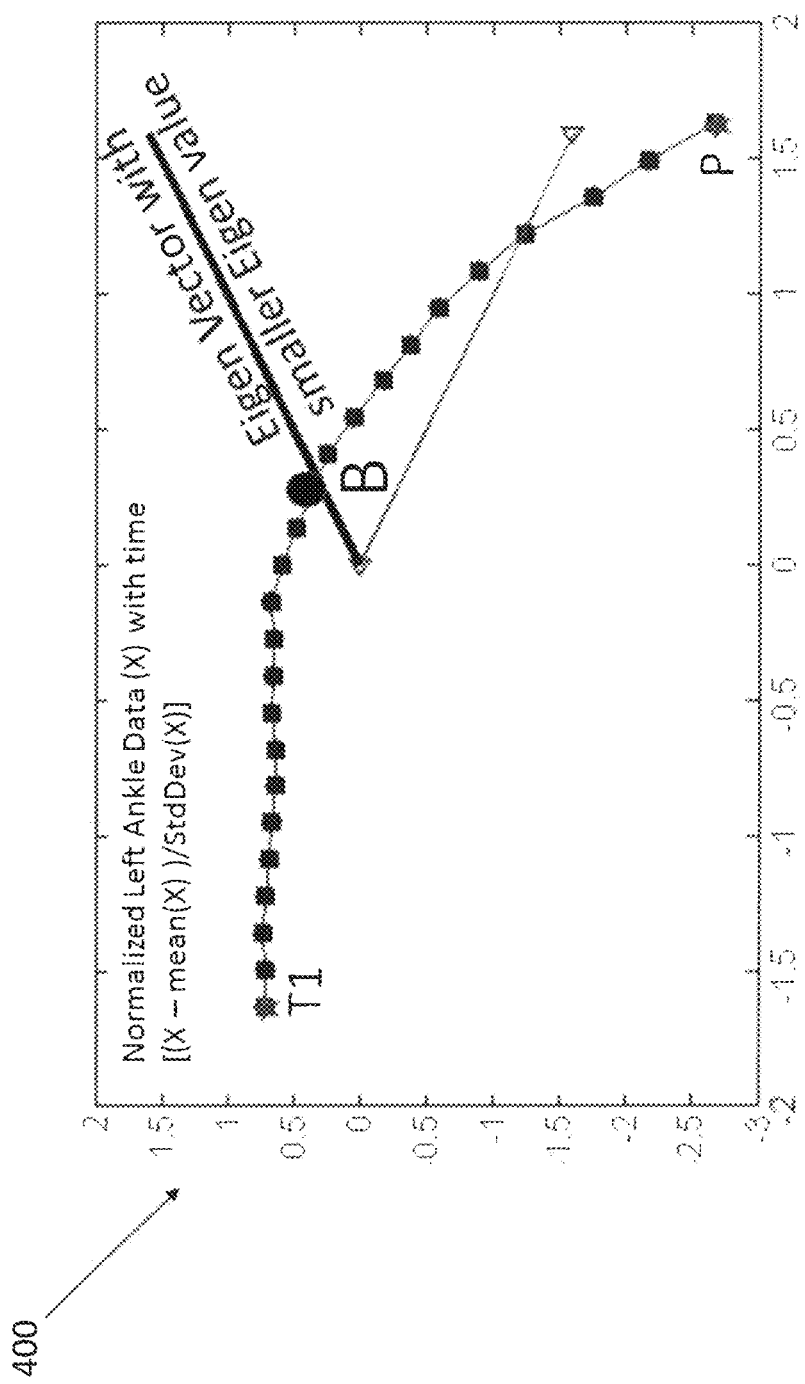
FIG. 6 shows a graphical representation of eigenvector based curvature analysis in accordance with an embodiment of the disclosure.

Further the eigenvalue decomposition of the matrix is computed. It should be appreciated that the principal component analysis (PCA) also uses the same principle to find the direction of maximum variance. The eigenvector (say, Emin) corresponding to the least eigenvalue provides the direction of minimum variance of the data and so reveals the direction towards curvature point. FIG. 6 shows the two direction vectors 400 obtained from eigen decomposition of covariance matrix. The curvature point "B" (between arc "T1" to "P") is obtained through computing minimum projection error of the eigenvector corresponding to smallest eigenvalue and it is computed using following equation:

$$\underset{r}{\operatorname{argmin}}\left[\vec{P}_r - (P_r, \hat{u})\hat{u}\right]$$

where $\vec{P}_r$ is the original signal value ($X_{AnkleLeft}$ (r)) at frame r (or time instance t); $\hat{u}$ is the unit vector along $\vec{E}_{min}$. The frame (point) "S1" is computed in similar manner, where the data between "P" and "T2" frames is used for eigenvector based curvature analysis. Finally, the stride length and time are measured by finding differences between displacement and time-stamp corresponding to "A" and "S" frames respectively. The curvature point "B" indicates the beginning of swing phase ("B" to "S1" w.r.t FIG. 5) preceded by a stance phase ("A" to "B" w.r.t FIG. 5). Thus all the four gait variables are modeled using following equations.

Stride length=$|X_{AnkleLeft}(\text{at ``}A\text{''})-X_{AnkleLeft}(\text{at ``}S1\text{''})|$, Stride time=$|\text{timestamp}(\text{at ``}A\text{''})-\text{timestamp}(\text{at ``}S1\text{''})|$, Swing time=$|\text{timestamp}(\text{at ``}S1\text{''})-\text{timestamp}(\text{at ``}B\text{''})|$, Stance time=$|X_{AnkleLeft}(\text{at ``}B\text{''})-X_{AnkleLeft}(\text{at ``}A\text{''})|$.

It should be appreciated that the proposed approach also provides an overview of gait velocity profile during swing and stance phase and yields two additional parameters namely maximum and minimum velocity corresponding to those phases.

Figure 7:
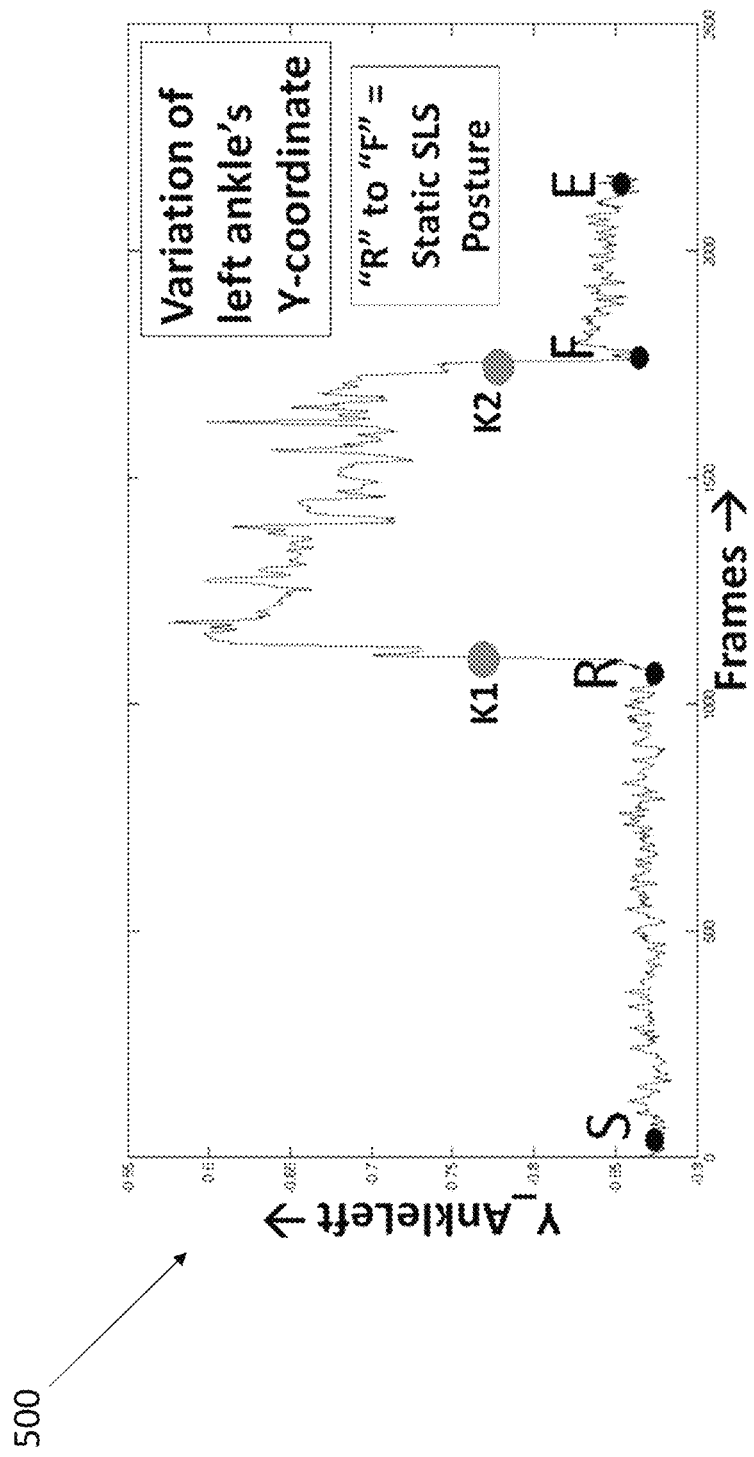
FIG. 7 shows a graphical representation of variation of $Y_{AnkleLeft}$ in accordance with an embodiment of the disclosure.

According to an embodiment of the disclosure, the static SLS measurement module 112 is used for analyzing the postural balance of the person. The postural balance is measured using the static SLS exercise. The static SLS exercise is all about raising one leg off the ground and maintaining body balance by the other leg. The experiment using static SLS exercise focuses on the variation in y-coordinate. The changes in the left ankle's y-coordinate (say, left leg is lifted) YAnkleLeft gives information about the precise timing when the person raises leg (here, left-leg) off the ground as shown in FIG. 7. FIG. 7 shows changes in YAnkleLeft at frames "R" and "F". The zone "R" to "F" is the desired zone of SLS posture. To put things into perspective, "R" is the frame where foot is flexed off the floor and "F" is the frame where it again touches the ground. The duration between "R" and "F" is considered as the static SLS duration.

In order to detect those frames, k-means clustering algorithm is employed to capture the variation in $Y_{AnkleLeft}$ over frames. It will in turn help in differentiating one leg stance portion (zone "R" to "F"). FIG. 7 also shows the output of k-means clustering algorithm i.e. frame "K1" and "K2" which are far away from the desired frames "R" and "F". Finally the proposed curvature analysis algorithm is used to find the curvature points "R" and "F" given data points in the region "S" to "K1" and "K2" to "E" respectively.

Figure 8:
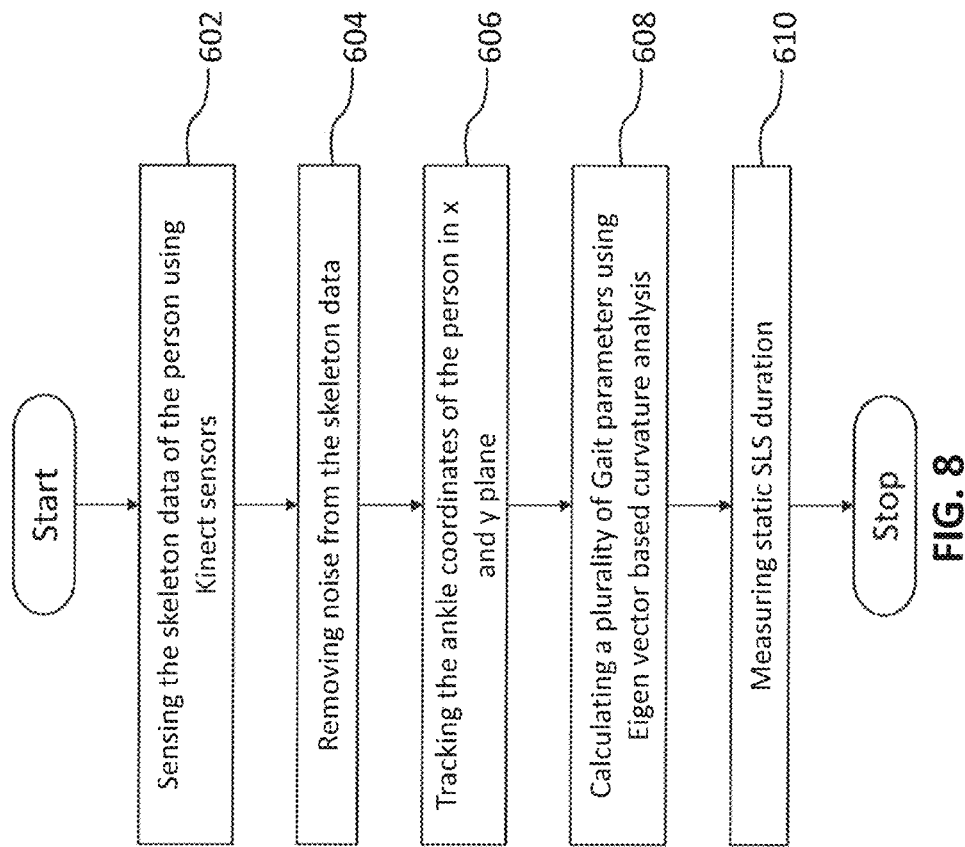
FIG. 8 is a flowchart illustrating steps involved for analyzing gait and postural balance of a person, in accordance with an embodiment of the disclosure.

In operation, a flowchart 600 illustrating the steps involved for analyzing the gait parameters and postural balance of the person is shown in FIG. 8. Initially, at step 602, skeleton data of the person is sensed using the Kinect sensor 102. Generally, the skeleton data sensed from the Kinect sensor 102 is full of noise. Therefore at step 604, the noise is removed from the skeleton data using the noise cleaning module 108. In the next step 606, ankle coordinates of the person are tracked along in the x and y plane. In the next step 608, a plurality of gait parameters are calculated using eigenvector based curvature analysis using gait parameter calculation module 110. And finally in the last step 610, static SLS measurement module 112 measures the It should be appreciated that the system 100 can be used for neuro-rehabilitation by analyzing the gait parameters. The system 100 is easy to use and can be installed at home as well as in clinic. Eigenvector based curvature detection is used to analyze the gait pattern with different speeds, which is quite accurate and robust. This also enables the possibility of tele-rehabilitation for patients at home.

According to an embodiment of the disclosure, the method for analyzing postural balance of a person can be validated with the help of following experimental findings.

Data Set Generation for Lower Body Gait Analysis

The experiments were performed on the six healthy participants (3 females and 3 males, age: 23.5-37 years old, height: 1.55 m-1.75 m, weight: 50-79 kg), with no neurological and no musculoskeletal disorders or symptoms.

Figure 9:
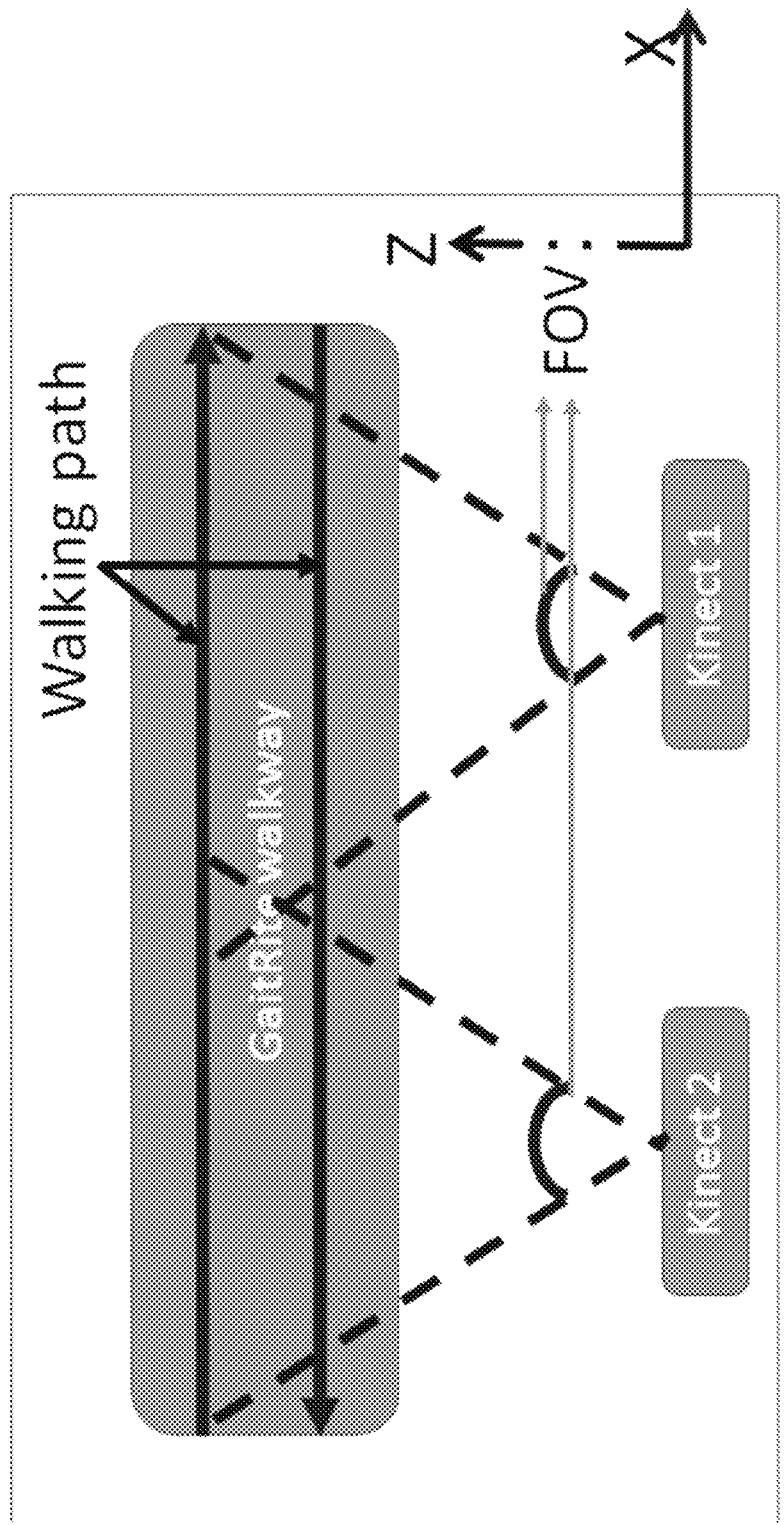
FIG. 9 is a top view of the layout of the walking path of the person standing in front of the Kinect sensor, in accordance with an embodiment of the disclosure.

Before starting the experiment, participants were introduced to the GAITRite system that computes the gait parameters. Ten sets of gait data were recorded with different walking speeds for every participant and the speed was randomly varied among the waking-trials (trial is defined as a complete walk from one end to another end of GAITRite). A one minute break was provided after each trial. Data is captured simultaneously using both GAITRite and Kinect setup consisting of two Kinect sensors (Version1 or V1). Time synchronization between the GAITRite system and Kinect controllers is accomplished by Network Time Protocol (NTP). Unlike previous Kinect-based gait analysis, the present setup uses two Kinects to cover the entire GAITRite walk-way of 8 meter(m), as each sensor has 3.52 m horizontal FOV. Two Kinects are positioned in parallel to the walk-way at 2 m-2.3 m distance from the subject and at a height of 1.5 m above the ground. They are placed 2.5 m apart to achieve minimum IR interference due to overlap of the FOVs. If the FOVs overlap, the depth data of both Kinect will be corrupted. Therefore, the data obtained from two Kinects are individually analyzed because transition from one FOV to another will contain IR interference. FIG. 9 depicts the typical layout of the Kinect sensors along with the approximate trace (top view) of the walking path used.

Data Set Generation for Static SLS Duration Measurement

Due to non-existence of any public dataset to estimate static SLS duration using skeleton data, dataset was created using Kinect V1. Thirty five healthy volunteers (age: 21-65 years, weight: 45 kg-120 kg & height: 1.42 m-1.96 m) with no pre-existing symptoms of neurological diseases, major orthopedic lesions or vestibular are examined for static single limb balance analysis. Participants perform the tests with bare feet, eyes open, arms on the hips looking straight ahead and standing at a distance of 2.1 m-2.4 m in front Kinect. For ground truth, time synchronized data capture has been carried out using Kinect and Force plate based setup.

Evaluation of Lower Body Gait Analysis

Figure 10:
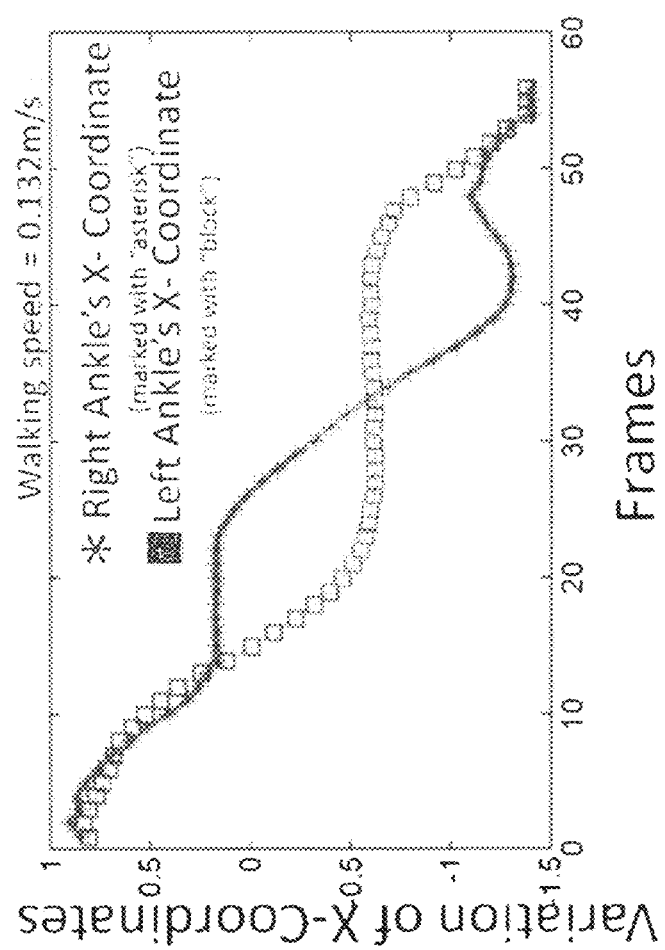
FIG. 10 shows a graphical representation of the Gait pattern of the person "L" with walking speed of 0.13 m/s, in accordance with an embodiment of the disclosure.
Figure 11:
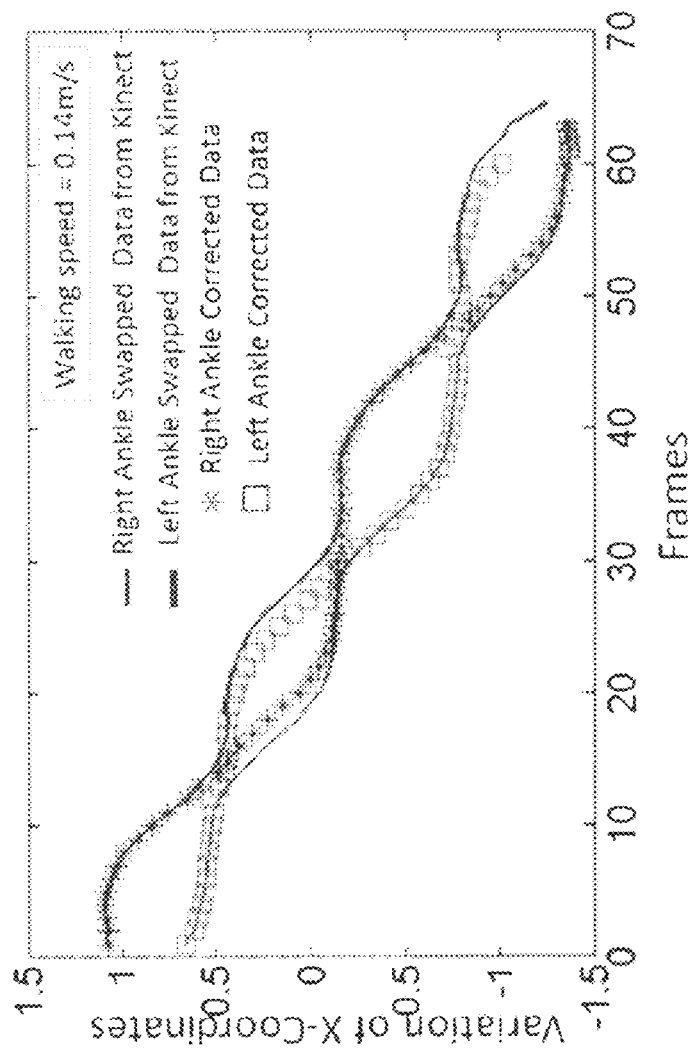
FIG. 11 shows a graphical representation of the Gait pattern with walking speed of 0.14 m/s, in accordance with an embodiment of the disclosure.

Stride length, stride time, stance time and swing time of left and right limbs are computed separately per walk for each Kinect sensor, to evaluate the performance of the proposed system. This is followed by a rigorous study of estimating mean absolute error (MAE), defined as $$MAE = \frac{1}{n}\sum_{i=1}^{n} |m_i - m'_i|$$

where $m_i$ and $m'_i$ correspond to the GAITRite (ground truth/GT) and Kinect measurements respectively, and n denotes the number of walking-trials taken. Table 1 represents the error between the computed (using the proposed method) gait parameters and GAITRite measurements. Table 1 also reveals that though Kinect measurements are very much closer to the ground truth, the measurement error increases with the walking speed. In fact, for both the legs, the magnitude of the error is significantly increased when average walking speed is greater than 0.13 m/s. It is mainly because Kinect often fails to capture minute variation of gait pattern for faster walking sequences, thus affecting nature of the displacement (i.e. $X_{AnkleLeft}$ or $X_{AnkleRight}$ with frames) curve. FIG. 10 legitimizes the noisy behavior of Kinect. Moreover, Kinect often fails to track left and right ankle accurately due to occlusion effect which also incorporates error in the analysis. FIG. 11 depicts how skeleton data of left and right ankles are swapped due to tracking inaccuracies. The average MAE for stride length, stride time, swing and stance time across all participants and for all walking speeds are 0.037 m, 0.15 s, 0.05 s, 0.041 s respectively.

Figure 12:
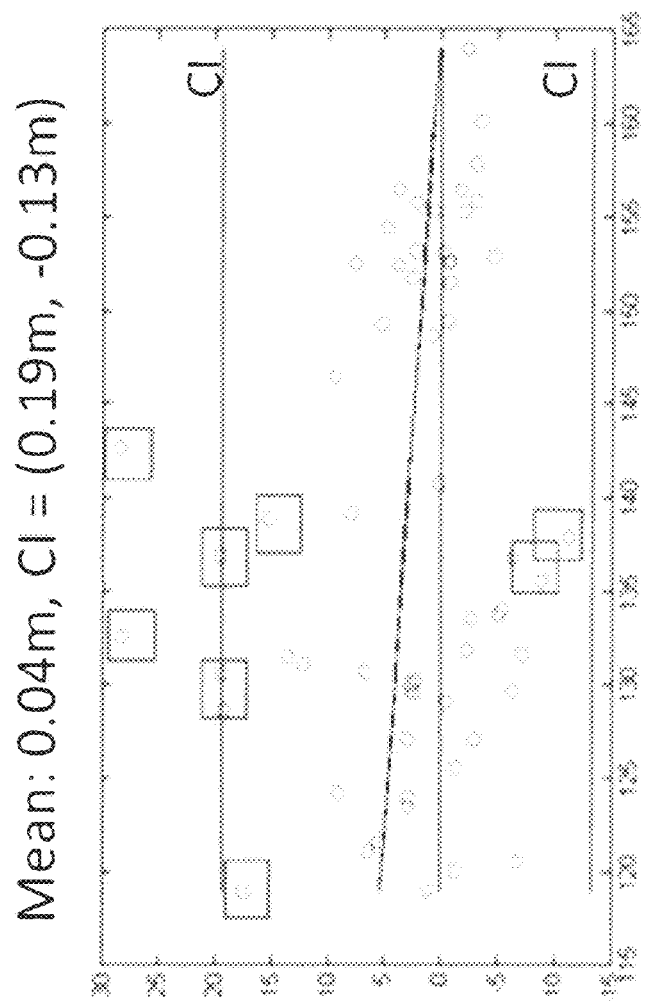
FIG. 12 shows a Bland-Altman plot for left leg's stride length, in accordance with an embodiment of the disclosure.
Figure 13:
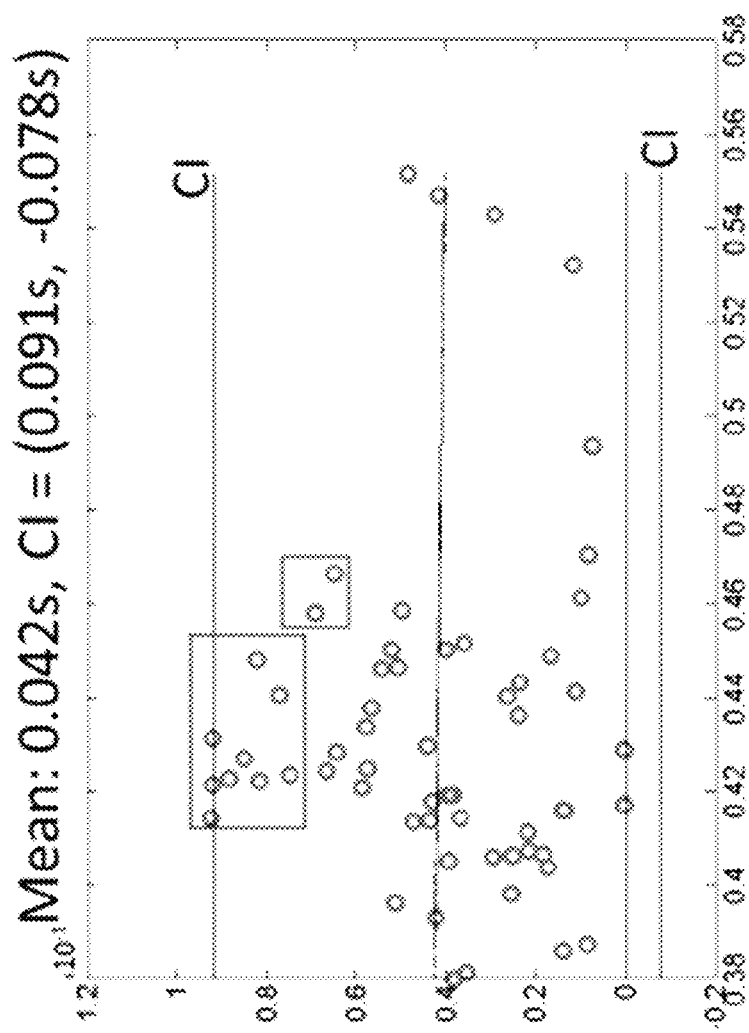
FIG. 13 shows a Bland-Altman plot for left leg's swing time, in accordance with an embodiment of the disclosure.

Apart from this, Bland-Altman agreement analysis is also carried out to realize whether any kind of bias exists between the measurements derived from two systems. FIG. 12 reveals that the squared points (trials) have relative high magnitude of errors which are mainly caused due to faster walking speeds. Besides, 95% of Confidence Interval (CI) of the slope does not show significant proportional bias for the stride length measurements. FIG. 13 depicts Bland Altman analysis for swing time measurement. The plot also portrays how the swing time is affected by walking speed (red squared points). The same analysis also holds good for stance and stride duration measurements. The eigenvector based curvature detection algorithm plays a key role in all of the measurements. To establish robustness of the approach, the proposed curvature analysis method is compared with an existing technique. The curvature points detected by state-of-the-art curvature detection algorithm denoted as [18]) are quite far (5 frames on an average) from the desired ones. This is due to the noisy skeleton data which the eigenvector based algorithm can handle better. This inaccuracy in curvature detection also affects the gait parameter extraction. Table 2 clearly validates claim for left leg, although the observation suits equally the right limb as well.

Static SLS duration measurement

The proposed solution is also capable of measuring static SLS duration from skeleton data. This experiment also aids to evaluate efficacy of devised curvature detection technique which plays a crucial role while analyzing stance and swing phase. The static SLS duration computed using the proposed technique is compared with the ground truth measurements made by the Force Platform based System. In the force based system, change in ground reaction force is mainly tracked to get the SLS duration. Comparison between the proposed method and the state-of-the-art curvature detection algorithm (denoted as [18]) keeping the standard ground truth (GT) system as reference is illustrated by Table 3.

TABLE 3

Camparison of [18] and our method considering force platform based system as ground truth (GT) for 35 subjects
Error (mean ± std) in static SLS duration measurement

| Our proposed method~GT (in seconds) | [18]~GT (in seconds) |
| --- | --- |
| 0.26 ± 0.3 | 0.66 ± 0.34 |

In view of the foregoing, it will be appreciated that the present disclosure provides a method and system to for finding and analyzing gait parameters and postural balance of a person using a Kinect system. The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

TABLE 1

Performance evaluation of our system with respect to GAITRite

Error (MAE) in measurements (% error presented in bracket)

| Walking speed | Stride length (m) | | Stride time (s) | | Stance time (s) | | Swing time (s) | |
| --- | --- | --- | --- | --- | --- | --- | --- | --- |
| | Left Leg | Right Leg | Left Leg | Right Leg | Left Leg | Right Leg | Left Leg | Right Leg |
| Normal | 0.031 (2.3%) | 0.027 (2.1%) | 0.148 (13.7%) | 0.142 (12.9%) | 0.047 (6.4%) | 0.053 (7.3%) | 0.051 (11.9%) | 0.031 (8.23%) |
| Slow (<0.04 m/s) | 0.029 (2.2%) | 0.034 (2.5%) | 0.131 (11.9%) | 0.140 (12.7%) | 0.091 (5.3%) | 0.049 (6.6%) | 0.029 (7.4%) | 0.025 (6.4%) |
| Fast (>0.13 m/s) | 0.053 (3.9%) | 0.047 (3.5%) | 0.171 (15.1%) | 0.159 (14.4%) | 0.084 (12.2%) | 0.063 (9.33%) | 0.060 (15.4%) | 0.052 (13.3%) |

TABLE 2

Comparsion of our method and [18] with respect to GAITRite for left leg

Error (MAE) in measurements (% error presented in bracket)

| Walking speed | Stride length (m) | | Stride time (s) | | Stance time (s) | | Swing time (s) | |
| --- | --- | --- | --- | --- | --- | --- | --- | --- |
| | Our | [18] | Our | [18] | Our | [18] | Our | [18] |
| Normal | 0.031 (2.3%) | 0.043 (3.1%) | 0.148 (13.7%) | 0.168 (15.5%) | 0.047 (6.4%) | 0.049 (6.8%) | 0.051 (11.9%) | 0.089 (28.7%) |
| Slow (<0.04 m/s) | 0.029 (2.2%) | 0.067 (3.1%) | 0.131 (11.9%) | 0.137 (12.7%) | 0.091 (5.3%) | 0.035 (4.9%) | 0.029 (7.4%) | 0.040 (12.9%) |
| Fast (>0.13 m/s) | 0.053 (3.9%) | 0.233 (17.4%) | 0.171 (15.1%) | 0.188 (17.7%) | 0.084 (12.2%) | 0.0950 (13.2%) | 0.060 (15.4%) | 0.083 (26.7%) |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, hulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example. The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for determining postural balance of a person, the method comprising processor implemented steps of:
    capturing a skeleton data of the person, wherein the skeleton data comprises spatiotemporal variations of an ankle joint data of the person in a x plane, a y plane and a z plane;
    removing a plurality of noises from the captured skeleton data using a noise cleaning module, wherein the plurality of noises comprises one or more of errors, and wherein the plurality of noises is removed by:
        converting the captured skeleton data into a set of features related to a physical structure of the person;
        computing static features of the physical structure in each frame of the captured skeleton data; and
        tracking changes in the static features based on a previous and a following frames of each frame of the captured skeleton data;
    tracking ankle coordinates of the person from the captured skeleton data only in the x-plane and the y-plane;
    determining a plurality of gait parameters of the person using the tracked ankle coordinates of the person by:
        obtaining a velocity profile of the tracked ankle coordinates;
        computing curvature points based on the velocity profile, wherein the curvature points are two points which indicate a beginning of two consecutive stance phases for a given leg;
        detecting peak and trough regions from the velocity profile and obtaining a set of data points in the peak and trough regions;
        computing a covariance matrix of standardized data, wherein the standardized data is obtained by calculating mean and standard deviation of the set of data points; and
        performing a first eigenvector based curvature analysis by computing an eigenvalue decomposition of the covariance matrix to obtain a curvature point indicative of a beginning of a swing phase for the leg, wherein an eigenvector corresponding to a least eigenvalue provides a direction of minimum variance of the set of data points and reveals a direction towards the curvature point indicative of the beginning of said swing phase; wherein the plurality of gait parameters are determined by using the obtained curvature point indicative of the beginning of said swing phase, the curvature points of the beginning of two consecutive stance phases, and the obtained set of data points in the peak and trough regions of the velocity profile; and measuring a static single limb stance (SLS) duration of the person by:
   capturing variations of a left ankle and a right ankle of the person in the tracked ankle coordinates of the person from the captured skeleton data in the x-plane and the y-plane; and
   performing a second eigenvector based curvature analysis on the captured the variations in the tracked ankle coordinates to determine two negative curvature points, wherein a duration between the determined negative curvature points is the static SLS duration.

2. The method of claim 1, wherein the peak and trough regions are detected by applying a peak and trough detection algorithm to the velocity profile of the person.

3. The method of claim 1, wherein a k-means clustering algorithm is employed to capture the variations of the left ankle and the right ankle of the person in the tracked ankle coordinates of the person over each frame for measuring the static SLS duration of the person.

4. The method of claim 1, wherein the plurality of gait parameters include stride length, stride time, swing time and stance time.

5. A system for determining postural balance of a person, the system comprises:
   a 3D motion sensor for capturing a skeleton data of the person, wherein the skeleton data comprises spatiotemporal variations of an ankle joint data of the person in a x plane, a y plane and a z plane;
   a noise cleaning module for removing a plurality of noises from the captured skeleton data, wherein the plurality of noises comprises one or more of errors, and wherein the plurality of noises is removed by:
      converting the captured skeleton data into a set of features related to a physical structure of the person;
      computing static features of the physical structure in each frame; and
      tracking changes in the static features based on previous and following frames;
   a memory; and
   a processor in communication with the memory, wherein the processor is further configured to perform the steps of:
   tracking ankle coordinates of the person from the captured skeleton data only in the x-plane and the y-plane;
   determining a plurality of gait parameters of the person using the tracked ankle coordinates of the person by:
      obtaining a velocity profile of the tracked ankle coordinates;
      computing curvature points based on the velocity profile, wherein the curvature points are two points which indicate a beginning of two consecutive stance phases for a given leg;
      detecting peak and trough regions from the velocity profile and obtaining a set of data points in the peak and trough regions;
      computing a covariance matrix of standardized data, wherein the standardized data is obtained by calculating mean and standard deviation of the set of data points; and
      performing a first eigenvector based curvature analysis by computing an eigenvalue decomposition of the covariance matrix to obtain a curvature point indicative of a beginning of a swing phase for the leg, wherein an eigenvector corresponding to a least eigenvalue provides a direction of minimum variance of the set of data points and reveals a direction towards the curvature point indicative of the beginning of said swing phase; wherein the plurality of gait parameters are determined by using the obtained curvature point indicative of the beginning of said swing phase, the curvature points of the beginning of two consecutive stance phases, and the obtained set of data points in the peak and trough regions of the velocity profile; and
   measuring a static single limb stance (SLS) duration of the person by:
      capturing variations of a left ankle and a right ankle of the person in the tracked ankle coordinates of the person from the captured skeleton data in the x-plane and the y-plane; and
      performing a second eigen vector based curvature analysis on the captured the variations in the tracked ankle coordinates to determine two negative curvature points, wherein a duration between the determined negative curvature points is the static SLS duration.

6. A non-transitory computer-readable medium having embodied thereon a computer program for determining postural balance of a person, by executing the steps comprising:
   capturing a skeleton data of the person, wherein the skeleton data comprises spatiotemporal variations of an ankle joint data of the person in a x plane, a y plane and a z plane;
   removing a plurality of noises from the captured skeleton data using a noise cleaning module, wherein the plurality of noises comprises one or more of errors, and wherein the plurality of noises is removed by:
      converting the captured skeleton data into a set of features related to a physical structure of the person;
      computing static features of the physical structure in each frame; and
      tracking changes in the static features based on previous and following frames;
   tracking ankle coordinates of the person from the captured skeleton data only in the x-plane and the y-plane;
   determining a plurality of gait parameters of the person using the tracked ankle coordinates of the person by:
      obtaining a velocity profile of the tracked ankle coordinates;
      computing curvature points based on the velocity profile, wherein the curvature points are two points which indicate a beginning of two consecutive stance phases for a given leg;
      detecting peak and trough regions from the velocity profile and obtaining a set of data points in the peak and trough regions;
      computing a covariance matrix of standardized data, wherein the standardized data is obtained by calculating mean and standard deviation of the set of data points; and performing a first eigenvector based curvature analysis by computing an eigenvalue decomposition of the covariance matrix to obtain a curvature point indicative of a beginning of a swing phase for the leg, wherein an eigenvector corresponding to a least eigenvalue provides a direction of minimum variance of the set of data points and reveals a direction towards the curvature point indicative of the beginning of said swing phase; wherein the plurality of gait parameters are determined by using the obtained curvature point indicative of the beginning of said swing phase, the curvature points of the beginning of two consecutive stance phases, and the obtained set of data points in the peak and trough regions of the velocity profile; and measuring a static single limb stance (SLS) duration of the person by:

capturing variations of a left ankle and a right ankle of the person in the tracked ankle coordinates of the person from the captured skeleton data in the x-plane and the y-plane; and performing a second eigenvector based curvature analysis on the captured the variations in the tracked ankle coordinates to determine two negative curvature points, wherein a duration between the determined negative curvature points is the static SLS duration.

* * * * *